United States Patent
Sparbier et al.

(10) Patent No.: US 10,144,946 B2
(45) Date of Patent: *Dec. 4, 2018

(54) **MASS SPECTROMETRIC RAPID DETECTION OF *SALMONELLA***

(75) Inventors: Katrin Sparbier, Bremen (DE); Ulrich Weller, Köln (DE); Markus Kostrzewa, Lilienthal (DE)

(73) Assignee: Bruker Daltonik GmbH, Bremen (DE)

( * ) Notice: Subject to any disclaimer, the term of this patent is extended or adjusted under 35 U.S.C. 154(b) by 6 days.

This patent is subject to a terminal disclaimer.

(21) Appl. No.: 13/102,085

(22) Filed: May 6, 2011
(Under 37 CFR 1.47)

(65) Prior Publication Data
US 2012/0107864 A1    May 3, 2012

(30) Foreign Application Priority Data
May 7, 2010   (DE) .................. 10 2010 019 869

(51) Int. Cl.
*C12Q 1/04*     (2006.01)
*G01N 33/68*   (2006.01)

(52) U.S. Cl.
CPC ........... *C12Q 1/04* (2013.01); *G01N 2560/00* (2013.01); *Y02A 50/451* (2018.01)

(58) Field of Classification Search
CPC .............................. C12Q 1/04; G01N 33/6848
See application file for complete search history.

(56) References Cited

U.S. PATENT DOCUMENTS

| | | | |
|---|---|---|---|
| 4,920,063 A | * | 4/1990 | Ward, Jr. ............... 435/7.35 |
| 7,391,017 B2 | | 6/2008 | Kostrzewa et al. |
| 2002/0192676 A1 | | 12/2002 | Madonna et al. |
| 2005/0061967 A1 | | 3/2005 | Shvartsburg et al. |
| 2006/0177824 A1 | | 8/2006 | Procop |
| 2008/0009029 A1 | | 1/2008 | Govorun et al. |
| 2009/0068706 A1 | | 3/2009 | Freudenschuss et al. |
| 2010/0248298 A1 | | 9/2010 | Kostrzewa et al. |

OTHER PUBLICATIONS

Menzel et al., Purification of the putA Gene Product, The Journal of Biological Chemistry, 1981, vol. 256, pp. 9755-9761.*
Ruelle et al., Rapid identification of environmental bacterial strains by matrix-assisted laser desorption/ionization time-of-flight mass spectrometry, Rapid Communications in Mass Spectrometry, 2004, vol. 18, pp. 2013-2019.*

(Continued)

*Primary Examiner* — Rosanne Kosson
(74) *Attorney, Agent, or Firm* — O'Shea Getz, P.C.

(57) ABSTRACT

The invention relates to the detection of specified, flagellated bacteria, particularly *Salmonella*, in food and stool. A single culturing period of about 12 to 24 hours in a liquid nutrient medium without agitation is combined with a position-selective sampling of the flagellated microbes from the liquid of the culture, after which a mass spectrometric detection method is used which recognizes the target bacteria in mixtures. A second culture step is only necessary in exceptional cases. A species-selective or genus-selective culture medium is advantageous. Positional selection becomes possible because these bacteria use their flagella to counteract sedimentation by chemotaxis, and they collect near the surface. This provides a low-cost detection method that is several days faster than conventional methods

12 Claims, 1 Drawing Sheet

(56) References Cited

OTHER PUBLICATIONS

Stuart et al., Isolation of *Salmonellae* by Selective Motility Systems, Applied and Environmental Microbiology, 1965, vol. 13, pp. 365-372.*

Sauer et al., Mass spectrometry tools for the classification and identification of bacteria, Nature Reviews Microbiology, Jan. 2010, vol. 8, pp. 74-82.*

Amy et al., Precise excision and secondary transposition of TnphoA in non-motile mutants of a *Salmonella enterica serovar* Enteritidis clinical isolate, FEMS Microbiology Letters, 2005, vol. 245, pp. 263-269.*

Berg et al., Selection of motile nonchemotactic mutants of *Escherichia coli* by field-flow fractionation, Proceeding of the National Academy of Sciences, 1991, vol. 88, pp. 8145-8148.*

Old et al., "Selection of fimbrate transductants of *Salmonella typhimurium* dependent on motility," J Bacteriol 107(3): 655-658, 1971.*

Dieckmann et al., "Rapid Classification and Identification of *Salmonellae* at the Species and Subspecies Levels by Whole-Cell Matrix-Assisted Laser Desorption Ionization-Time of Flight Mass Spectrometry", Applied and Environmental Microbiology, Dec. 2008, vol. 74, No. 24, p. 7767-7778.

Swaminathan et al., "Rapid Detection of *Salmonellae* in Foods by Membrane Filter-Disc Immunoimmobilization Technique", Journal of Food Science, vol. 43, No. 5, 1978, p. 1444-1447.

IS 15187 (2002) : Water Quality—Detection of *Salmonella* Species [FAD 14: Drinks and Carbonated Beverages].

Andrews et al., "*Salmonella*", US Food and Drug Administration Bacteriological Analytical Manual, Chapter 5, Apr. 2003, available at http://www.fda.gov/Food/FoodScienceResearch/LaboratoryMethods/ucm070149.htm.

Laszlo et al., "Aerotaxis in *Salmonella typhimurium*: Role of Electron Transport", Journal of Bacteriology, Feb. 1981, p. 990-1001.

GB Office Action dated Feb. 26, 2015.

Shioi et al., "Oxygen as Attractant and Repellent in Bacterial Chemotaxis", Journal of Bacteriology, Jul. 1987, p. 3118-3123.

GB Office Action dated Sep. 29, 2015.

* cited by examiner

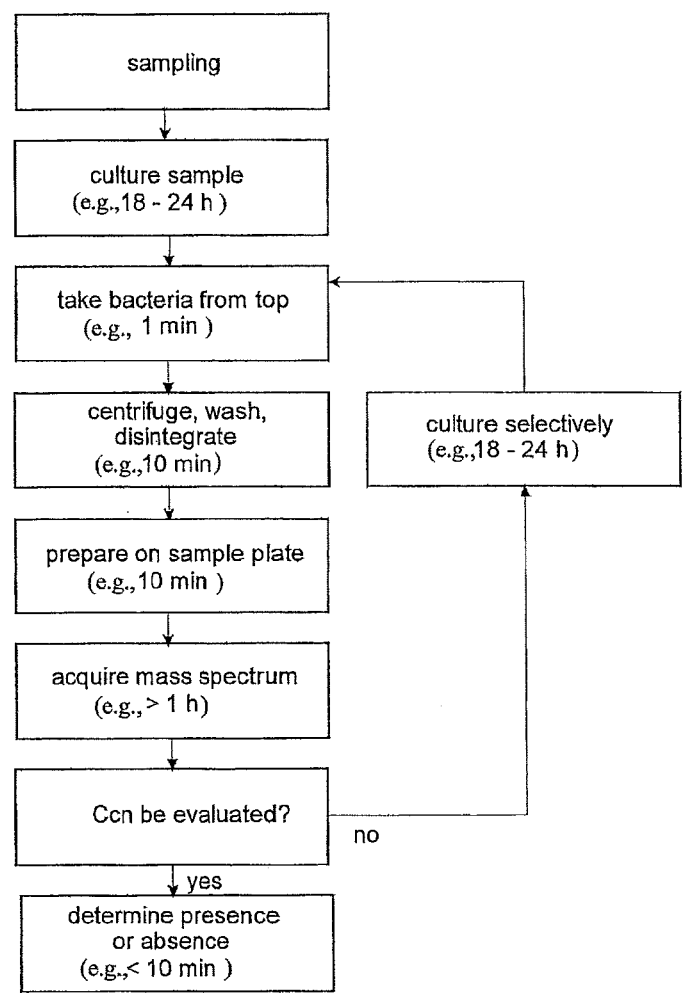

MASS SPECTROMETRIC RAPID DETECTION OF *SALMONELLA*

PRIORITY INFORMATION

This patent application claims priority from German Patent Application 10 2010 019 869.2 filed on May 7, 2010, which is hereby incorporated by reference.

FIELD OF THE INVENTION

The invention relates to mass spectrometry, and in particular to the mass spectrometric detection of flagellated bacteria, such as for example *Salmonella*, in food and stool.

BACKGROUND OF THE INVENTION

Many bacteria and many pathogenic bacteria in particular, are flagellated. The flagella and their action mechanism in the case of the *E. coli* species of bacteria have been precisely investigated. The flagella propel the bacteria, a process which is usually controlled by chemotaxis and enables them to find favorable living conditions. Repellants are avoided and attractants are followed by occasional statistical changes in direction (tumbling) after straight motions of controlled length. The control is based on concentration gradients of the attractants or repellants. Successive stimulus responses during the straight motion cause these straight motions to be continued if the conditions are favorable or to be discontinued, and a new direction tried, if the development of the concentrations is unfavorable. One percent concentration changes in a concentration range of more than five orders of magnitude can be perceived.

The rapid detection of pathogenic bacteria is important in food monitoring, in the search for sources of infection, and also to identify the type of infection contracted by a patient in order to combat the cause.

*Salmonella* is a genus of flagellated bacteria that belongs to the family of Enterobacteriaceae and is closely related to the *Escherichia* genus (usually also flagellated). According to the latest consensus only two species belong to the *Salmonella* genus, namely *S. enterica* and *S. bongori*, the former being subdivided into six sub-species with 2500 serovars nowadays. Most of the *Salmonella* species are pathogenic for humans and animals and may cause mild, but often severe, typhoidal or paratyphoidal bowel infections. They can survive for prolonged periods of time outside the human or animal organism (e.g., in dried feces demonstrably for 2.5 years), but are destroyed at 55° Celsius in one hour, at 60° Celsius in half an hour, making it relatively simple to disinfect equipment and food.

*Salmonella* infection occurs through oral ingestion, due to poor hygiene, infected water, or infected food. *Salmonella* infections are notifiable if they occur either endemically, or in places where nursing care is provided or food is produced.

The detection of *Salmonella* in the stool of patients, and also in food, is by nature always urgent. Known methods are slow or expensive. For example, they generally take at least two days, and usually three to five days.

A method which is both inexpensive and fast is urgently required. It should preferably provide a definitive result on the day after the sample was taken, at the latest. For food it is additionally desirable to be able to process many samples simultaneously without the analysis time and cost increasing significantly.

The conventional identification of microorganisms is usually based on standard methods that include of a series of consecutive culturing steps. Suitable selective broths or agar media are used, depending on the microorganism to be identified and on the particular application. After culturing, the actual identification of the individual colonies is performed either biochemically using the so-called "API test" or serologically by latex agglutination. These methods provide results after two days at the earliest, but sometimes may require five days. Two commonly used known methods will be briefly described.

To identify *Salmonella* in stool samples, a pea-sized stool sample is incubated overnight in ten milliliters of selective broth at 37° Celsius. Strongly selective methods must always be used here since stool samples always contain *E. coli* in large quantities also. The selective culture media used include selenite broth (enriches *Salmonella*, inhibits *Escherichia*), Rappaport-Vassiliadis broth (RVS, inhibits *E. coli*, but cannot be used for *S. typhi* or *S. paratyphi*), tetrathionate broth or Müller-Kauffmann tetrathionate broth with novobiocin (MKTTn, also inhibits *E. coli*). After this initial culture step, one milliliter of the liquid culture is plated on selective agar (e.g., XLD agar). After incubating overnight at 37° Celsius, the individual colonies obtained are characterized either biochemically (by the so-called "API test"), mass spectrometrically or serologically by agglutination. Characterization using "API test" requires a further 24-hour incubation of the microorganisms at 37° Celsius. With agglutination or mass spectrometry the result can be read off more or less directly. However, identifying *Salmonella* by the standard method takes at least two to three days.

In most countries, official standard methods exist for detecting *Salmonella* in food. In Germany, for instance, they are described in § 64 "Collection of Official Analytical Methods (ASU) according to German Food Law (LFGB: Lebensmittel-, Bedarfsgegenstände- and Futtermittelgesetzbuch)". As an example, the L 00.00-20 method used to detect *Salmonella* will be described below. The usual detection procedure is to transfer 10 to 25 grams of the food under investigation to a non-selective pre-enrichment broth (buffered peptone water) in order to reactivate and, where necessary, propagate any *Salmonella* present (peptone water makes it possible to resuscitate sublethally damaged *Salmonella*). After incubating for 20 hours at 37° Celsius, two main enrichment cultures are started from the pre-enrichment culture. The main enrichment cultures contain selective media (Müller-Kauffmann Tetrathionate Broth (MKTTn) and Rappaport-Vassiliadis Broth (RVS)) and are inoculated with 0.1 to 1 milliliter of pre-enrichment culture, depending on the broth. MKTTn cultures are incubated at 37° Celsius and RVS cultures at 41.5° Celsius for 24 hours. A smear from each of these main enrichment cultures is made on an XLD agar and a second selective agar (a Rambach agar, for example). After incubating the plates for 24 hours at 37° Celsius, suspect colonies are investigated for *Salmonella*. If no suspect colonies have grown, the result is negative for *Salmonella*. To characterize possible suspect colonies further, they are subcultured on a CASO agar (24 hours, 37° Celsius). *Salmonella* is then detected using either "API test" or latex agglutination. This standard method for *Salmonella* takes four to five days.

Detection methods from molecular biology, which have major advantages over these conventional methods, have been known for a number of years. In the food sector, to identify *Salmonella* a method of identifying many microorganisms by DNA analysis after PCR amplification (polymerase chain reaction) is disclosed in U.S. Published Patent Application 2006 177 824 A1. In contrast to the standard methods of culturing, this method can provide a result after only one to two days and thus saves valuable time. Its disadvantage includes the relatively high cost per culture, taking into account the fact that food inspections usually involve many samples each time (often a few hundred). Furthermore PCR is prone to interference, depending on the sample. Extensive positive and negative controls have to be carried out to validate the results.

A further method from molecular biology is based on a mass spectrometric analysis of microbe-specific molecular cell components. This method is superior to conventional methods in terms of specificity (true-negative rate), sensitivity (true-positive rate), other error rates, and particularly in terms of cost and analytical speed.

The process of generating mass spectra of the components of the cultured microbes usually starts with a cleanly isolated colony on a solid, usually gelatinous nutrient medium or a centrifuge sediment (pellet) from a liquid nutrient medium. A tiny quantity of microbes is transferred from the selected colony or sediment to the mass spectrometric sample support, using a small swab, such as a wooden tooth pick. An acidified solution of a conventional matrix substance is then sprinkled onto this sample, the matrix substance being used for subsequent ionization of the microbe components by matrix-assisted laser desorption (MALDI). The acid of the matrix solution attacks the cell walls and weakens them; the organic solvent penetrates the microbial cells, causing them to burst by osmotic pressure, and releases the soluble proteins. The sample is then dried by evaporating the solvent, which causes the dissolved matrix material to crystallize. The soluble proteins and, to a lesser extent, other substances of the cell also are thus embedded into the matrix crystals.

Instead of transferring whole microbes by swabs, the microbes cleaned by washing can also be disintegrated in vitro, in a centrifuge tube, for example, where strong acids can be used to destroy the microbial cell wall. Centrifuging separates the insoluble components such as cell walls so that they can no longer interfere with the mass spectrometric analysis. Around one microliter of the solution is applied to the mass spectrometric sample support and dried there. This analysis sample is then coated with a suitable matrix solution and dried again. During the drying process, protein molecules are incorporated into the small matrix crystals which form. These disintegration produce mass spectra which are practically identical to those of the usual preparation on sample supports, but are cleaner; they exhibit less interfering background and are therefore better suited to detecting pathogens, in mixtures with other microbes also.

The sample preparations dried on sample supports, i.e., the matrix crystals with the embedded protein molecules, are bombarded with pulsed UV laser light in a mass spectrometer, thus creating ions of the protein molecules that can then be measured, with separation according to the mass of the ions in the mass spectrometer. This type of ionization by matrix-assisted laser desorption is usually referred to as Matrix-Assisted Laser Desorption and Ionization (MALDI). It is preferable to use MALDI time-of-flight mass spectrometers for this purpose. Several types of crystalline organic acids can be used as matrix substances: HCCA(α-cyano-4-hydroxycinnamic acid), for example.

Nowadays, the mass spectra of the microbe proteins are scanned in the linear mode of these time-of-flight mass spectrometers, i.e., without using an energy-focusing reflector, because this mode gives a particularly high detection sensitivity, although the mass resolution and the mass trueness of the spectra from time-of-flight mass spectrometers in reflector mode is considerably better. The lack of reproducibility of the desorption and ionization processes for the generation of the ions means that the masses of the individual mass signals shift slightly from spectrum to spectrum. These shifts in the mass scales of the repeat spectra can be readjusted with respect to each other using a method described in U.S. Pat. No. 7,391,017, before homogeneous groups of repeat spectra are combined to form a sum spectrum, which is then used as a reference spectrum or sample spectrum. The mass scales of sample and reference spectra can also be adjusted with respect to each other by this mass scale adjustment program. This means that smaller mass tolerance intervals can be used for the determination of matching mass signals during the similarity analysis, which is crucial for a good identification, even if it takes some time.

The mass spectrum of a microbial isolate is the frequency profile of the ions of the soluble cell components, separated according to mass The ions are predominantly protein ions. The mass spectra are usually acquired in the mass range from 2,000 to 20,000 daltons; the most useful information for identifications is found in the mass range from around 3,000 daltons to 15,000 daltons. Each laser light pulse produces a single mass spectrum, which is measured in less than 100 microseconds but contains the signals of only a few hundred to a few thousand ions. In order to obtain more reliable and less noisy mass spectra, a few tens to a few thousands of these individual mass spectra are added together to form a sum mass spectrum. The individual mass spectra can preferably originate from different parts of the sample preparation or even from different sample preparations. The term "mass spectrum of a microbe", or more simply "microbe spectrum", refers to this sum mass spectrum. The acquisition of such a microbe spectrum takes only a few seconds due to the high laser bombardment rates (currently up to two kilohertz). A sample support plate with 48 or even 384 samples may be automatically measured in less than half an hour.

The profile of the proteins reproduced by each of these microbe spectra is characteristic of the species of microbe in question because each species produces its own, genetically predetermined proteins, each having their own characteristic masses. The abundances of the individual proteins in the microbes, in as much as they can be measured mass spectrometrically, are also genetically predetermined to a large extent because their production is controlled by other proteins, and they depend only slightly on the nutrient medium or the degree of maturity of the colony. The protein profiles are characteristic of the microbes in the same way that fingerprints are characteristic of humans. This makes it possible to identify the microbes by a similarity analysis with reference spectra from a reference library.

The spectra acquired are evaluated with programs provided by the manufacturers of the mass spectrometers. These programs are based on similarity analyses between a measured microbe spectrum and reference mass spectra from specially validated spectral libraries. This is done by calculating a similarity index score for each reference spectrum. If the highest index score exceeds a specified similarity threshold, it is clear proof that the microbe species belonging to the corresponding reference spectrum is present. There are special similarity thresholds for the assignment of microbes to families, genera or species.

It must be emphasized that the mass spectrometric method has so far been mainly used for the identification of unknown bacteria. Bacteria isolates from well-separated colonies on agar plates have usually been used for the sample preparation. The identification of two, at best three, bacterial species in a mixture of these two or three species is disclosed in German Patent DE 10 2009 007 266.7. A great strength of the mass spectrometric method which has not been utilized so far is its ability to detect the presence of a target bacterial species in somewhat more complex mixtures of five, ten or more bacterial species unambiguously and reliably if the signature of this target species is still detectable in the mass spectrum of the mixture at all. It is not necessary, and often not possible, to identify all the bacteria of the mixture. Even the absence of a target bacterial species can be identified with certainty if a signal of the target bacterial species which is definitely to be expected is missing in at least one location in the mixture spectrum. Special evaluation programs enable the presence or absence of target bacteria to be detected unambiguously and reliably even if they amount to only one to ten percent of the mixture, depending on the complexity of the mixture. This type of detection of a target bacterial species in mixtures has not been elucidated so far, especially since the evaluation programs commercially available to date are not designed for this task.

SUMMARY OF THE INVENTION

According to an aspect of the present invention, a mass spectrometer detects a target bacteria, even in mixtures, and preferably limits the culturing to only one step in a suitable broth without agitation, while exploiting the spatial separation of different species of microbe in the broth by a selective sampling of the target bacteria from the culture for a further analysis. Particularly advantageous is a culture that favors the target bacteria by using selective culture broths, particularly with the aim of inhibiting closely related genera, e.g., to detect *Salmonella* as opposed to *Escherichia*. If the culture is carried out gently, without the usual agitation, a natural sedimentation of unflagellated microbes in the culture liquid occurs. The target bacteria, on the other hand, preferentially collect in the top portion of the culture liquid by virtue of the active propulsion by their flagella. The collection of the target bacteria in the upper portion of the liquid culture may be assisted by introducing repellants specific to the target bacteria near the bottom. Thus if the microbes for further analysis are taken from the top layer of the liquid, the *Salmonella* are enriched compared to all unflagellated bacteria, and also compared to all flagellated bacteria that do not react to the repellant.

The liquid taken from the top of the broth is centrifuged; the bacteria of the pellet are washed and disintegrated in the centrifuge tube. The dissolved proteins are transferred to MALDI sample supports, mixed or coated with matrix substance and measured mass spectrometrically. The presence of the target bacteria may be detected directly in the mass spectra with suitable evaluation programs. Only if the mass spectrum becomes too complex does a second culturing stage in a selective medium become necessary.

These and other objects, features and advantages of the present invention will become more apparent in light of the following detailed description of preferred embodiments thereof, as illustrated in the accompanying figures.

BRIEF DESCRIPTION OF THE DRAWING

FIG. 1 illustrates the steps of a method for detecting *Salmonella* in a sample.

DETAILED DESCRIPTION OF THE INVENTION

A single culturing period of about 12 to 24 hours in a liquid nutrient medium (a "broth") is combined with a position-selective sampling of flagellated microbes from the culture, after which a mass spectrometric detection method is used to recognize the pathogenic target bacteria in mixtures. A second culture step is generally only necessary in exceptional cases. A species-selective or genus-selective culture is advantageous. Positional selection becomes possible because these bacteria use their flagella to counteract sedimentation by chemotaxis, therefore, at least in the period of the last hours, the culturing should be performed without agitation.

A detection method is depicted in FIG. 1.

The invention can be used for all types of flagellated bacteria; however the description shall discuss the method in the context of detecting *Salmonella*. Two examples of the detection method for *Salmonella* are specified below; they relate specifically to stool and to food samples.

In a first example, to analyze stool samples for *Salmonella*, a pea-sized piece of stool is put into about 10 milliliters of selective broth and incubated for about 18 to 24 hours at about 37° Celsius without agitation. Selenite broth, RVS broth or MKTTn broth can be used as the selective media. Simple tetrathionate broth is not suitable for the detection because the *Salmonella* is too strongly overgrown with *E. coli* if the start numbers of *Salmonella* are low.

The method involves taking about 150 microliters from the very top of the selenite broth, diluting in one milliliter of water and centrifuging at about 13,000 revolutions per minute for about two minutes in a micro centrifuge. The supernatant is discarded. The pellet is resuspended in one milliliter of water and centrifuged again under identical conditions. The supernatant is again discarded and the pellet is washed once more with one milliliter of water.

For both the RVS and the MKTTn broth, about one milliliter is taken from the top of the tube and centrifuged and washed under the conditions described above.

The pellets thus obtained are dried in air and subsequently lysed in about 20 to 50 microliters of about 70 percent formic acid, the exact amount depending on the pellet size. The same amount of acetonitrile is then added to dissolve the proteins released. Insoluble cell components are separated off by centrifuging for about two minutes at about 13,000 revolutions per minute in the micro centrifuge. One microliter of the lysate is pipetted onto a MALDI sample support. After drying, the sample is coated with about one microliter of HCCA solution. The HCCA solution contains about 10 milligrams of α-cyano-4-hydroxycinnamic acid per milliliter of solvent, which includes about 50% acetonitrile, 2.5% trifluoroacetic acid and 47.5% water. HCCA serves as the matrix for the subsequent ionization of the proteins by matrix-assisted laser desorption. After drying, the samples are measured mass spectrometrically on the sample support.

The spectra acquired can be evaluated with programs which the mass spectrometer manufacturers provide with the instruments ("Bruker Bio-Typer", for example). These programs are based on similarity analyses between the measured mass spectra of the microbe proteins and reference mass spectra from spectral libraries. Similarity index scores are calculated, and if these index scores exceed specified similarity values, *Salmonella* is unambiguously detected. If *Salmonella* occurs in the ranking list of the ten most similar reference spectra, this is a clear indication that it is present in the sample.

The use of evaluation programs that can detect the presence of target bacteria in mixture spectra using reference mass spectra of the target bacteria may further increase the certainty of detection of *Salmonella* in the sample. In particular, the absence of the target bacteria may be identified by the absence of mass signals of the target bacteria that are definitely to be expected in the mixture spectrum. In mixtures of proteins from different bacteria, some protein signals of proteins that are hard to ionize, are suppressed by concurrent proteins of other bacteria. Therefore, it may be favorable to study the protein signals of *Salmonella* within different types of mixtures in order to find those signals which do occur in any case. Only if one of these must-be-there signals is lacking, the absence can be detected with certainty.

To detect presence or absence of *Salmonella*, however, the mixture mass spectrum must not be so complex that it is more or less completely obscured with mass signals. The requirement can be that around 50 percent, or even around 70 percent, of the mixture mass spectrum is not occupied by with mass signals. If the mixture mass spectrum is not empty enough, a further culture in a selective nutrient medium must be performed in order to enhance the target bacteria in preference to the other bacteria.

After incubation, it takes only about an hour to process the samples and to carry out the measurements, even for larger numbers of samples. This method generally produces an unambiguous result as to whether or not *Salmonella* is present in the stool sample in less than 24 hours, thus saving one to two days of analysis time compared to conventional methods.

In a second example, to detect *Salmonella* directly from food, 10 to 25 grams of the coarsely chopped food is incubated in about 225 ml of buffered peptone water for about 20 hours at approximately 37° Celsius without agitation, the food being prevented from rising to the surface by a plastic clamping grid. Depending on the secondary flora in the material under analysis, *Salmonella* may be detected directly from this pre-enrichment culture by mass spectrometric analysis. This is done by taking about one milliliter from the very top portion of the pre-culture and centrifuging it for about two minutes at about 13,000 revolutions per minute in the microcentrifuge. The supernatant is discarded and the pellet resuspended in about one milliliter of around 70 percent ethanol and centrifuged under the same conditions. After the supernatant has been discarded, the pellet is dried. As described above for the stool samples, the pellet is now lysed in about 20 to 50 microliters of about 70 percent formic acid, depending on the size of the pellet, and then the same amount of acetonitrile is added. Here, also, insoluble cell components are separated by centrifuging for about two minutes in the microcentrifuge. MALDI samples are prepared from the lysate, and these samples are measured in the mass spectrometer. The samples are not usually contaminated with several species of bacteria (unless contaminated with feces). In these cases the evaluation programs detect directly from the pre-culture whether *Salmonella* is present.

A selective main enrichment step only needs to be carried out if there is strong secondary flora which is visible in the mass spectrum and detected by the evaluation program. This step involves transferring about one milliliter into MKTTn broth or about 0.1 milliliter into RVS broth and incubating for about 24 hours at around 37° Celsius. About half a milliliter is then taken from the top portion of the culture and prepared as described above as mass spectrometric MALDI samples. The analysis time here is usually one day, or at most two, instead of the four to five days for current standard methods.

Surprisingly, the *Salmonella* collects in the uppermost layer of the culture liquid to a high degree. This may be explained by the fact that not only does the culture liquid contain particular attractants, but also the samples, e.g., stool or food, often also contain repellants, for example salts in unpleasant concentrations. Since the movement of the *Salmonella* is controlled only by concentration gradients, the attractants in the culture liquid cannot alone attract the *Salmonella* to the surface because the attractants have the same concentration everywhere (unless they were to be used up to a noticeable degree, which is not the case). If, however, repellants spread slowly in the liquid by diffusion, this generates a concentration gradient that drives the *Salmonella* to the surface. It is also possible that a higher concentration of oxygen in the uppermost region acts as an attractant; nothing seems to be known about the chemotaxis of the *Salmonella* by oxygen, however.

This spatial separation can be increased further if certain repellants, in the form of initially undissolved small crystals, for example, are added to the culture near the bottom in addition to the samples of stool or food. Phenol is one example of a repellent for *Salmonella*. Small crystals lying on the bottom gradually dissolve, and the dissolved repellants diffuse into the culture liquid and thus generate a concentration gradient which drives the target bacteria to the surface. On the other hand, an extra attractant applied near the surface (e.g., serine for *Salmonella*) can attract the target bacteria to the surface.

The preparation of the MALDI samples on the mass spectrometric sample support is performed here as described above. The evaluation of the measured mass spectra of the mixtures of bacteria also follows the description above. Even if the complexity of the mixture mass spectra means a second culture in a selective nutrient medium has to follow the first culture, this detection method for *Salmonella* in food is two to three days faster than conventional methods.

The mass spectra are preferably measured in time-of-flight mass spectrometers specially equipped for ionization by matrix-assisted laser desorption (MALDI). The MALDI ionization process has the advantage that essentially only singly-charged ions of the proteins are generated; this means that the mass spectrum is drawn out over a wide region of the charge-related masses m/z, and can be evaluated simply and well. Ionization by other ionization methods, such as electrospray ionization (ESI), and also the use of other mass spectrometers shall not be excluded here, however.

Although the present invention has been illustrated and described with respect to several preferred embodiments thereof, various changes, omissions and additions to the form and detail thereof, may be made therein, without departing from the spirit and scope of the invention.

What is claimed is:
1. A method for detecting the presence or absence of flagellated target bacteria in stool or food samples comprising microbes that may or may not comprise flagellated target bacteria, comprising the steps:
   (a) introducing a stool or food sample into a liquid nutrient medium;
   (b) incubating the liquid nutrient medium with the sample for a predetermined time for culturing the microbes;
   (c) removing a sample of liquid from the surface of the liquid nutrient medium, wherein the liquid nutrient medium is not agitated at least during a period of time prior to removing the sample of liquid;
   (d) directly after being removed from the liquid nutrient medium, centrifuging, washing and disintegrating the microbes from the removed sample of liquid; and then
   (e) detecting the target bacteria by mass spectrometric analysis of the constituents of the disintegrated microbes.

2. The method of claim 1, wherein the liquid nutrient medium is selective for the flagellated target bacteria.

3. The method of claim 1, wherein the predetermined time is about 12 to 24 hours.

4. The method of claim 1, wherein the constituents of the disintegration are ionized by matrix-assisted laser desorption.

5. The method of claim 4, wherein the constituents of the disintegration are prepared with the matrix substance α-cyano-4-hydroxycinnamic acid (HCCA) on a sample support plate for the mass spectrometer.

6. The method according to claim 1, wherein the target bacteria are of the genus *Salmonella*.

7. The method according to claim 1, wherein the target bacteria are driven to the surface of the liquid nutrient medium by the addition of repellants and/or attractants.

8. The method according to claim 1, wherein a further selective culture is performed if a mixture mass spectrum acquired in mass spectrometric analysis of step (e) is too densely populated with mass signals.

9. The method according to claim 8, wherein the further selective culture is performed if more than 50 percent of the mixture mass spectrum is occupied by mass signals.

10. The method according to claim 1, wherein the presence of the target bacteria in the microbe mixture is determined by the fact that all the mass signals of a reference mass spectrum that are definitely to be expected are also in fact present in the mixture mass spectrum acquired in mass spectrometric analysis of step (e).

11. The method of claim 1, wherein the absence of the target bacteria in the microbe mixture is determined by the fact that mass signals of a reference mass spectrum that are definitely to be expected are not present in a mixture mass spectrum acquired in mass spectrometric analysis of step (e).

12. A method for detecting the presence of flagellated target bacteria in stool or food samples comprising microbes that may or may not comprise flagellated target bacteria, comprising the steps:
  (a) introducing a stool or food sample into a liquid nutrient medium;
  (b) incubating the liquid nutrient medium with the sample for a predetermined time for culturing the microbes;
  (c) removing a sample of liquid from the surface of the liquid nutrient medium, wherein the liquid nutrient medium is not agitated at least during a period of time prior to removing the sample of liquid;
  (d) centrifuging, washing and disintegrating the microbes from the removed sample of liquid without further isolation on agar plates; and
  e) detecting the target bacteria by mass spectrometric analysis of the constituents of the disintegrated microbes.

* * * * *